United States Patent
Zhong et al.

(10) Patent No.: US 12,049,418 B2
(45) Date of Patent: Jul. 30, 2024

(54) SEWAGE TREATMENT BIOLOGICAL AGENT AND PREPARATION METHOD AND APPLICATION THEREOF

(71) Applicant: Hunan Sanyou Environmental Protection Technology Co. LTD, Changsha (CN)

(72) Inventors: Yan Zhong, Changsha (CN); Dan Hou, Changsha (CN); Hongbo Han, Changsha (CN); Jing Yi, Changsha (CN)

(73) Assignee: Hunan Sanyou Environmental Protection Technology Co. LTD, Changsha (CN)

( * ) Notice: Subject to any disclaimer, the term of this patent is extended or adjusted under 35 U.S.C. 154(b) by 0 days.

(21) Appl. No.: 17/962,536

(22) Filed: Oct. 9, 2022

(65) Prior Publication Data
US 2023/0249999 A1    Aug. 10, 2023

(30) Foreign Application Priority Data
Oct. 9, 2021  (CN) .......................... 202111178156.5

(51) Int. Cl.
*C02F 3/34* (2023.01)
*C02F 3/12* (2023.01)
(Continued)

(52) U.S. Cl.
CPC ............... *C02F 3/348* (2013.01); *C02F 3/12* (2013.01); *C02F 11/02* (2013.01); *C12N 11/00* (2013.01);
(Continued)

(58) Field of Classification Search
CPC . C02F 3/348; C02F 3/12; C02F 11/02; C12N 11/00
(Continued)

(56) References Cited

U.S. PATENT DOCUMENTS 5,580,770 A  * 12/1996  DeFilippi ............... C02F 3/085
                                                   210/615
2009/0181434 A1*  7/2009  Aikens .................. C12M 23/24
                                                   435/320.1

FOREIGN PATENT DOCUMENTS

CN        1837361 A  *  9/2006
CN      106006950 A  * 10/2016
(Continued)

OTHER PUBLICATIONS

Yan et al, CN 110980960A, English Machine Translation, pp. 1-7 (Year: 2020).*
(Continued)

Primary Examiner — Claire A Norris
(74) Attorney, Agent, or Firm — Nitin Kaushik

(57) ABSTRACT

The present invention provides a sewage treatment biological agent and a preparation method and application thereof. The sewage treatment biological agent according to an embodiment of the present invention includes an induced nucleus. The induced nucleus has good bioaffinity. A microbial flora can be attached to the induced nucleus to achieve rapid growth. As the microbial flora gathers and grows on the induced nucleus, the granulation is gradually achieved by the sewage treatment biological agent to facilitate the sewage treatment. The microbial flora grows on the induced nucleus, and the growth process of microbial flora is a covering growth process which starts from the induced nucleus and gradually expands outward and centers on the induced nucleus. During the growth of microbial flora, extracellular polymers are secreted, which can further promote the granulation process by the sewage treatment biological agent.

7 Claims, 3 Drawing Sheets

(51) Int. Cl.
*C02F 11/02* (2006.01)
*C12N 11/00* (2006.01)

(52) U.S. Cl.
CPC ...... *C02F 2209/08* (2013.01); *C02F 2209/14* (2013.01); *C02F 2209/16* (2013.01); *C02F 2301/02* (2013.01); *C02F 2305/06* (2013.01)

(58) Field of Classification Search
USPC .................................................. 210/610, 615
See application file for complete search history.

(56) References Cited

FOREIGN PATENT DOCUMENTS

| | | | | |
|---|---|---|---|---|
| CN | 206266327 U | | 6/2017 | |
| CN | 107176702 A | * | 9/2017 | ............... C02F 3/00 |
| CN | 206940532 U | * | 1/2018 | |
| CN | 209507716 U | | 10/2019 | |
| CN | 209567871 U | | 11/2019 | |
| CN | 110980960 A | * | 4/2020 | ............... C02F 1/40 |
| CN | 106186284 B | * | 6/2020 | ............... C02F 3/00 |
| EP | 3009408 A1 | * | 4/2016 | ............. C02F 3/006 |

OTHER PUBLICATIONS

Ge et al, English Machine Translation CN 107176702 A, pp. 1-8 (Year: 2017).*

* cited by examiner

SEWAGE TREATMENT BIOLOGICAL AGENT AND PREPARATION METHOD AND APPLICATION THEREOF

CROSS-REFERENCE TO RELATED APPLICATIONS

The application claims priority to Chinese patent application No. 202111178156.5, filed on Oct. 9, 2021, the entire contents of which are incorporated herein by reference.

TECHNICAL FIELD

The present invention belongs to the technical field of sewage treatment, and specifically relates to a sewage treatment biological agent and a preparation method and application thereof.

BACKGROUND

With the increase of urban population, the problem of urban domestic sewage is becoming more and more obvious. The treatment technologies of municipal sewage can be divided into three types according to the mechanism of action: physical treatment, chemical treatment and biological treatment. According to the physical treatment method, the suspended pollutants are separated and recovered from the sewage by physical action, without changing the chemical properties of the pollutants in the treatment process. It mainly includes sieve filtration, gravity separation and centrifugal separation. According to the chemical treatment method, the dissolved and colloidal pollutants are separated and recovered from the sewage by chemical reaction and mass transfer, or converted into harmless substances. Common chemical treatment methods include chemical dosing, electrolysis, mass transfer, etc. According to the biological treatment method, by the metabolism of microorganisms, makes pollutants in a dissolved state or colloidal state, and some insoluble organic and even inorganic pollutants in the sewage are converted into stable and harmless substances, so that the sewage is purified.

In the biological treatment method, the activated sludge process has the advantages of simple process, flexible operation mode, low investment and convenient operation, and it is widely used in the field of municipal domestic sewage treatment. However, there are still some problems, such as loose sludge floc, poor settling performance and easy sludge expansion, which results in that the effluent nitrogen, phosphorus and other indicators are difficult to meet the more and more stringent sewage discharge standards.

Aerobic granular sludge is an aggregate particle derived from microorganisms under certain hydraulic shear force. The aerobic granular sludge has many advantages, such as regular and compact biological structure, high specific gravity, excellent settling rate and so on, and can be maintained at a high sludge concentration and volume load in the reactor, reducing or eliminating the secondary sedimentation tank to a large extent. In addition, the higher microbial diversity in the aerobic granular sludge has the potential to degrade organic carbon and remove nitrogen and phosphorus simultaneously. Compared with the traditional sewage treatment method by the traditional activated sludge process, the aerobic granular sludge method can simplify the process flow, reduce the floor area of sewage treatment system and cut the operation cost. Since researchers found aerobic granular sludge in an up-flow aerobic sludge bed reactor for the first time, they have cultivated aerobic granular sludge with different performances by using different operating mechanisms. Aerobic granular sludge technology is considered as one of the most promising biological sewage treatment technologies.

However, under the inflow condition of low concentration of municipal sewage, the aerobic granular sludge has a long start-up period, difficult granulation, an unstable structure and poor treatment effect, which limits the wide application of aerobic granular sludge technology in the municipal sewage treatment. In the related art, researchers propose that the formation of aerobic granular sludge can be promoted and the structural stability of granules can be improved by means of exogenous strengthening. At present, there are three kinds of exogenous strengthening, including metal ion strengthening, coagulant/coagulant aid strengthening and inert carrier strengthening. However, these strengthening methods not only increase the cost, but also fail to solve the problem of structural instability in the long-term operation of aerobic granular sludge.

SUMMARY

The present invention aims to solve at least one of the above technical problems existing in the prior art. To this end, the present invention provides a sewage treatment biological agent and a preparation method and application thereof.

The present invention also provides a preparation method for the above-mentioned sewage treatment biological agent.

The present invention also provides an application of the above-mentioned sewage treatment biological agent.

According to a first aspect of the present invention there is provided a sewage treatment biological agent comprising an induced nucleus on which a microbial flora grows, the induced nucleus comprising nutrient components required for the growth of the microbial flora, the volume of the induced nucleus being gradually reduced during the growth of the microbial flora.

One of the technical solutions of the present invention relating to the sewage treatment biological agent has at least the following beneficial effects.

The sewage treatment biological agent according to an embodiment of the present invention includes an induced nucleus. The induced nucleus has good bioaffinity. A microbial flora can be attached to the induced nucleus to achieve rapid growth. As the microbial flora gathers and grows on the induced nucleus, the granulation is gradually achieved by the induced nucleus to facilitate the sewage treatment.

In the sewage treatment biological agent according to the embodiment of the present invention, the microbial flora grows on the induced nucleus, and the growth process of microbial flora is a covering growth process which starts from the induced nucleus and gradually expands outward and centers on the induced nucleus. During the growth of microbial flora, extracellular polymers are secreted, which can further promote the granulation process by the sewage treatment biological agent.

According to the sewage treatment biological agent and microbial flora of the embodiments of the present invention, during the growth process of the microbial flora, the microbial flora close to the induced nucleus can use the induced nucleus as a nutrient source, effectively solving the premature cavitation of the inner nucleus which may be caused by mass transfer problems during the operation of the sewage treatment biological agent.

According to the sewage treatment biological agent of the embodiment of the present invention, the induced nucleus comprises nutrient components required for the growth of the microbial flora, and the volume of the induced nucleus is gradually reduced during the growth of the microbial flora. When the material of the induced nucleus is waste such as degradable plastics, waste utilization is achieved, which is beneficial to environmental protection and resource utilization of plastics.

According to the sewage treatment biological agent of the embodiment of the present invention, under the condition of low concentration of urban sewage inflow, the period of the granulation process of the sewage treatment biological agent is short, and it is easy to realize the granulation process. The structure of the sewage treatment biological agent is stable, and the treatment effect is good.

According to some embodiments of the invention, the induced nucleus has a three-dimensional helical structure.

According to some embodiments of the present invention, the three-dimensional helical structure has a length of 0.5-2.5 mm.

According to some embodiments of the present invention, the three-dimensional helical structure has pores distributed thereon.

The induced nucleus has a three-dimensional helical structure, which is beneficial to increase the specific surface area of the induced nucleus and provide more attachment sites for the microbial flora, so as to achieve the retention of activated sludge on the outer surface of the induced nucleus and the interior of the nucleus, and the rapid growth of the microbial flora attached to the surface of the induced nucleus. Meanwhile, the secretion of extracellular polymers by the microbial flora promotes the rapid granulation process of the microbial flora.

According to some embodiments of the invention, the density of the induced nucleus is greater than the density of the sewage.

The density of induced nucleus is greater than that of sewage, which is beneficial to the natural settling of sewage treatment biological agent. When the sewage treatment biological agent naturally settles in the sewage, the flow shear force can be applied to the outer edge of the particles during the downward and upward movement of the sewage by means of pulse inflow. The downward and upward flow shear force can screen the loose biological flocs on the outer edge of the biological flora attached by the induced nucleus in the sewage, and eliminate the loose biological flocs with poor settling performance, so as to promote the combination of induced nucleus and microbial flora and the formation of biological aggregation particles.

According to some embodiments of the invention, the three-dimensional helical structure has a length of 0.5-2.5 mm.

The length of the three-dimensional helical structure is 0.5-2.5 mm, with the function to facilitate the preparation of induced nucleus and control the granulation process.

According to some embodiments of the present invention, the preparation raw material of the induced nucleus comprises a degradable plastic.

Choosing degradable plastics as the induced nucleus can provide the needed nutrient components for the growth of microbial flora. In the growth process of microbial flora, the induced nucleus as the nutrient components will gradually reduce or even eventually disappear, realizing the re-use of waste, which is conducive to environmental protection and resource utilization and has good economic value.

Degradable plastics include degradable plastic raw materials and formed degradable lunch boxes, degradable mulching films, degradable packaging bags and degradable plastic fibers, and degradable medical materials, etc.

According to some embodiments of the present invention, the preparation raw materials of the induced nucleus include the following components in parts by weight:
a degradable plastic, 95-85 parts,
a catalyst, 1-5 parts;
a mineral powder, 2-5 parts;
a blowing agent, 2-5 parts.

Types of catalysts include amino acids, inorganic salts, vitamins, and the like, with the function to accelerate the process of membrane formation and granulation of microorganisms on the surface of induced nucleus.

Types of mineral powders include calcium powder, pyrite powder, and the like, with the function to regulate the density of induced nucleus. During the process of sewage treatment, the mineral powder, as an electron donor, plays the role of an alternative carbon source.

Types of foaming agents include sodium bicarbonate, sodium carbonate, azodicarbonamide, and the like, with the function to use the foaming principle to make the induced nucleus material of three-dimensional helical structure to be porous, so that the induced nucleus has a larger specific surface area and provides more attachment points for microorganisms.

The preparation raw materials of the induced nucleus includes, in addition to the catalyst, mineral powder and foaming agent, hydrophilic surface modifiers and other modifiers that promote microbial growth and attachment, including polyols, quaternary ammonium salts and sulfonates, and the like.

The preparation of the induced nucleus includes the following steps.

The recovered degradable plastic is melt and blended with a catalyst, a mineral powder and a foaming agent, then pelletized, extruded and shaped to obtain the induced nucleus.

According to a second aspect of the present invention, there is provided a preparation method for the sewage treatment biological agent as described above, the induced nucleus and activated sludge are mixed and then placed in a pulse up-flow reactor for membrane formation, hydraulic sieving and granulation.

According to some embodiments of the present invention, the sewage in the pulse up-flow reactor enters the pulse up-flow reactor in a pulse manner after being oxygenated and aerated, wherein the sewage has a COD of 100 mg/L-400 mg/L, an ammonia nitrogen of 15 mg/L-40 mg/L, and a total nitrogen of 15 mg/L-45 mg/L.

One of the technical solutions of the present invention relating to a preparation method for the sewage treatment biological agent has at least the following beneficial effects.

According to the preparation method for the above-mentioned sewage treatment biological agent, there are a wide range of induced nucleus raw materials. The preparation conditions are not severe, is simple and feasible, and the method can be achieved without using additional expensive equipment.

According to some embodiments of the present invention, the microbial flora in the sewage includes, but is not limited to, *rhodococcus, burkholderia, myxococcus, xanthomonas, rhodobacter, rhizobium, pseudomonas, sphingomonas, Sphingobacterium, flavobacterium, clostridium, Nitrospira*, and verrucomicrobia.

According to some embodiments of the present invention, the preparation method further comprises forming a flow shear force from the bottom to the top in the pulse up-flow reactor by pulse inflow of 5 s to 40 s.

According to some embodiments of the present invention, the preparation method further includes applying a flow shear force to the outer edge of the particles during the cultivation by the sewage moving from the bottom to the top.

The flow shear force from the bottom to the top can screen the loose biological flocs on the outer edge of the biological flora with induced nucleus attached in the sewage, improve the settling performance of the aggregated particles of the biological flora with the induced nucleus, and promote the combination of the induced nucleus and the microbial flora.

A third aspect of the present invention provides an application of the above-described sewage treatment biological agent in municipal sewage treatment.

According to the provisions of GB18918, in municipal sewage refers to the domestic sewage of urban residents, the drainage of institutions, schools, hospitals, commercial service institutions and various public facilities, and the industrial sewage allowed to be discharged into urban sewage collection system, and primary rainwater.

Activated sludge is the end sludge of an aerobic tank of a municipal sewage treatment plant.

DETAILED DESCRIPTION OF THE EMBODIMENTS

Hereinafter, embodiments of the present invention will be described in detail with reference to examples, but the present invention is not limited to these examples.

Example 1

Figure 1:
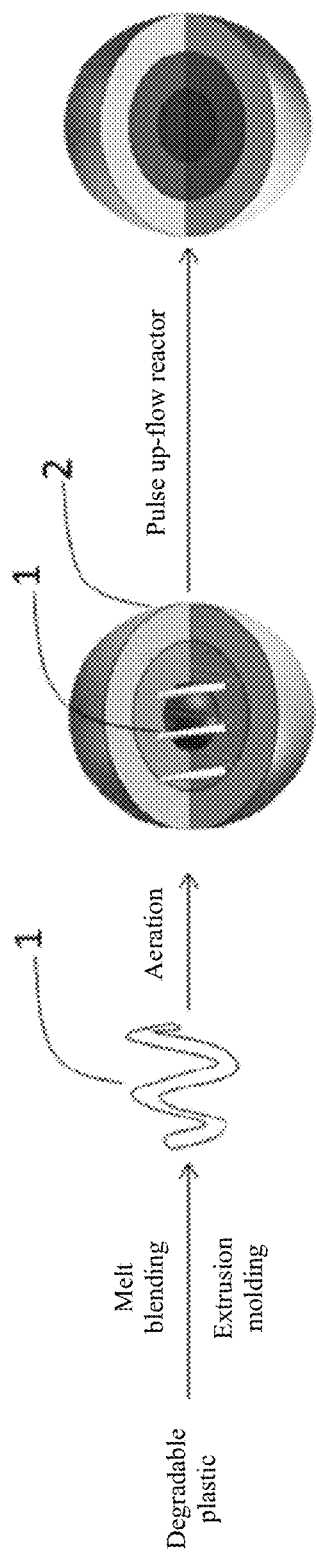
FIG. 1 is a process flow diagram for the preparation of a sewage treatment biological agent.

In this example, a sewage treatment biological agent is prepared, and the specific process is as follows.
(1) Preparation of induced nucleus: the recovered degradable plastic is melt and blended and then pelletized and extruded to form a three-dimensional helical structure. The procedure is shown in FIG. 1. In FIG. 1, 1 is an induced nucleus with a three-dimensional helical structure, and 2 is an aggregate of microbial colonies attached to the induced nucleus for growth.

Figure 2:
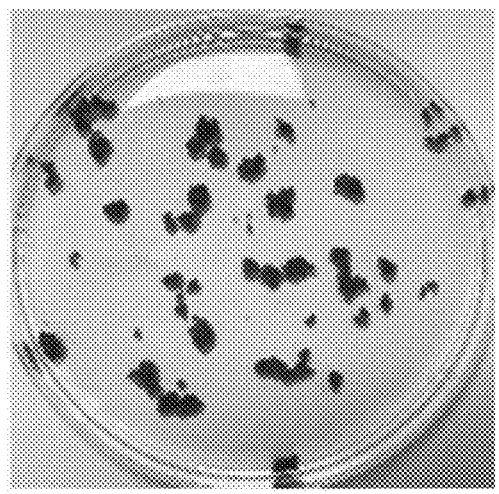
FIG. 2 shows a visual observation result for an induced nucleus prepared in Example 1.
Figure 3:
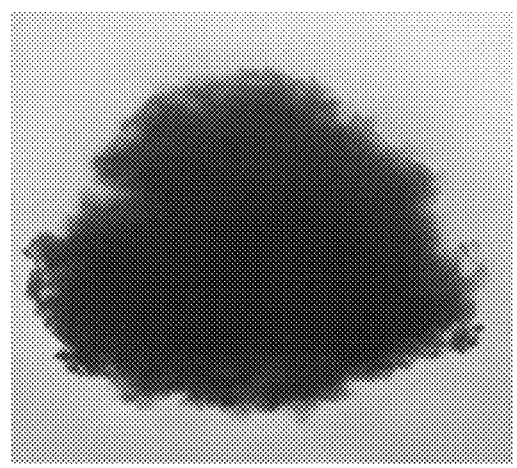
FIG. 3 shows a microscopic observation result for the induced nucleus prepared in Example 1.

The length of the induced nucleus of the three-dimensional helical structure is 1-2 mm. The resulting induced nucleus is prepared as shown in FIGS. 2 and 3. FIG. 2 shows a visual observation result, and FIG. 3 shows a microscopic observation result. As can be seen from FIGS. 2 and 3, the aggregate structure of the microbial flora attached to the induced nucleus for growth is compact.

Among them, the degradable plastics are recycled degradable plastic bags and degradable mulching films.

The preparation raw material of the induced nucleus is a degradable plastic.
(2) Preparation of sewage treatment biological agent:

The prepared induced nucleus is placed in the sewage for cultivation. The sewage enters the pulse up-flow reactor in a pulse manner after being oxygenated and aerated, wherein the sewage has a COD of 100 mg/L-400 mg/L, an ammonia nitrogen of 15 mg/L-40 mg/L, and a total nitrogen of 15 mg/L-45 mg/L.

The determination of the culture endpoint can be judged according to the particle size and settling rate.

One way to determine the culture endpoint is to consider the culture complete when the settling velocity of the sewage treatment biological agent is much higher than that of the floc sludge.

After 50 days of culture, it is observed that the sewage treatment biological agent is observed to be 1.5-3 mm, granular, compact and excellent in settling performance.

Example 2

In this example, a sewage treatment biological agent is prepared, and the specific process is as follows.
(1) Preparation of induced nucleus: the recovered degradable plastic is melt and blended with a catalyst and then pelletized and extruded to form a three-dimensional helical structure.

The length of the induced nucleus of the three-dimensional helical structure is 1-2 mm.

The degradable plastics are degradable plastic bags and degradable mulching films, and the catalyst is phenylalanine.

Preparation raw materials of the induced nucleus include the following components in parts by weight.
a degradable plastics, 95 parts;
a catalyst, 5 parts.
(2) Preparation of sewage treatment biological agent:

The prepared induced nucleus is placed in the same sewage and reactor as in Example 1 for cultivation.

After 42 days of culture, it is observed that the sewage treatment biological agent is observed to be 1.5-3 mm, granular, compact and excellent in settling performance.

Example 3

In this example, a sewage treatment biological agent is prepared, and the specific process is as follows.
(1) Preparation of induced nucleus: the recovered degradable plastic, the catalyst and the mineral powder are melt and blended and then pelletized and extruded to form a three-dimensional helical structure.

The length of the induced nucleus of the three-dimensional helical structure is 1-2 mm.

The degradable plastics are degradable packaging bags and degradable mulching films. The catalyst is phenylalanine. The mineral powder is calcium powder and pyrite powder, with the mass ratio of calcium powder to pyrite powder being 1:4.

Preparation raw materials of the induced nucleus include the following components in parts by weight.
a degradable plastics, 92 parts;
a catalyst, 5 parts;
a mineral powder, 3 parts.
(2) Preparation of sewage treatment biological agent:

The prepared induced nucleus is placed in the same sewage and reactor as in Example 1 for cultivation.

After 35 days of culture, it is observed that the sewage treatment biological agent is observed to be 1.5-3 mm, granular, compact and excellent in settling performance.

Example 4

In this example, a sewage treatment biological agent is prepared, and the specific process is as follows.

(1) Preparation of induced nucleus: the recovered degradable plastic is melt and blended with a catalyst, a mineral powder and a foaming agent, and then pelletized and extruded to form a three-dimensional helical structure.

The length of the induced nucleus of the three-dimensional helical structure is 1-2 mm.

The degradable plastics are degradable plastic bags and degradable mulching films. The catalysts are amino acid and inorganic salt. The mineral powder is calcium powder and pyrite. The foaming agent is sodium carbonate. The mass ratio of calcium powder to pyrite powder is 1:4.

Preparation raw materials of the induced nucleus include the following components in parts by weight.

a degradable plastics, 90 parts;
a catalyst, 5 parts;
a calcium powder, 3 parts;
a foaming agent, 2 parts.

(2) Preparation of sewage treatment biological agent:

The prepared induced nucleus is placed in the same sewage and reactor as in Example 1 for cultivation.

After 30 days of culture, it is observed that the sewage treatment biological agent is observed to be 1.5-3 mm, granular, compact and excellent in settling performance.

Comparative Example 1

In this comparative example, a sewage treatment biological agent is prepared, which differs from Example 1 in that no degradable plastic is used and polyethylene is used in the raw material for the preparation of the induced nucleus.

Comparative Example 2

In this comparative example, a sewage treatment biological agent is prepared, which differs from Example 1 in that no degradable plastic is used in the raw material for the preparation of the induced nucleus, and activated carbon particles are used.

Test Example

The sewage treatment performance of the sewage treatment biological agents prepared in Examples 1 to 4 and Comparative Examples 1 and 2 is tested. After the sewage treatment biological agent is cultured completely, the water in and out of the system is sampled and tested. The detection indicators include water quality indicators such as COD, ammonia nitrogen and total nitrogen, and sludge indicators such as MLSS and SVI, which evaluate the capacity of the cultured sewage treatment biological agent to treat municipal sewage.

Before treatment, in the sewage, COD is 100 mg/L-400 mg/L, ammonia nitrogen is 15 mg/L-40 mg/L, and total nitrogen is 15 mg/L-45 mg/L.

After the sewage treatment biological agent is cultured completely, the water samples at the inlet and outlet are taken for testing continuously for 30 days. The data in Table 1 is the average value of the removal efficiency of each pollutant for continuous 30 days.

The results of the treatment are shown in Table 1.

TABLE 1

| | COD removal rate (%) | Ammonia nitrogen removal rate (%) | Total nitrogen removal rate (%) | Culture period/d |
|---|---|---|---|---|
| Example 1 | 93.5 | 96.9 | 78.5 | 50 |
| Example 2 | 95 | 97 | 80.1 | 42 |
| Example 3 | 96.8 | 98.5 | 84.3 | 35 |
| Example 4 | 97.9 | 98.9 | 85.5 | 30 |
| Comparative Example 1 | 92.3 | 96.5 | 68.4 | 60 |
| Comparative Example 2 | 93.5 | 95.4 | 65.1 | 65 |

According to the test results in Table 1, the induced nucleus prepared with degradable plastics can provide attachment points for microbial growth, accelerate the granulation process of sewage treatment biological agent, and enhance the removal of organic matter and nitrogen in the sewage by the sewage treatment biological agent. The culture period of sewage treatment biological agent with basic degradable plastics as induced nucleus is 50d, and the removal rates of COD, ammonia nitrogen and total nitrogen are 93.5%, 96.9% and 78.5%, respectively. According to Comparative Examples 1 and 2, the sewage treatment biological agent prepared by using polyethylene and activated carbon particles as an inert material to induced nucleus has a loose structure. The removal rate of pollutants in the sewage is much lower than that of the sewage treatment biological agent in the examples. In addition, there is a phenomenon that the sewage treatment biological agent disintegrates in the treatment process. By blending and granulating the degradable plastics with the catalyst, mineral powder and foaming agent by melting, the new induced nucleus can further shorten the culture period of sewage treatment biological agent. The prepared sewage treatment biological agent has compact structure and good settling performance. In addition, the addition of catalyst and mineral powder can effectively improve the removal efficiency of organic matter and nitrogen by the sewage treatment biological agent.

Although the present invention has been described in detail with reference to the examples, the present invention is not limited to the above examples. Various changes may be made within the scope of knowledge of those skilled in the art without departing from the spirit of the present invention.

What is claimed is:

1. A sewage treatment biological agent, comprising: an induced nucleus and a microbial flora grown on the induced nucleus, the induced nucleus comprising nutrient components required for the growth of the microbial flora, wherein the sewage treatment biological agent is obtained by a process comprising the step of growing the microbial flora to induce a gradual reduction in the volume of the induced nucleus, wherein the induced nucleus has a three-dimensional helical structure, a density of the induced nucleus is greater than a density of sewage to be treated using the sewage treatment biological agent, wherein a preparation raw material of the induced nucleus comprising the following components in parts by weight:

a degradable plastic, 95-85 parts;
a catalysts, 1-5 parts; wherein the catalyst comprises amino acids, inorganic salts, or vitamins;
a mineral powder, 2-5 parts; wherein the mineral powder comprises calcium powder and pyrite powder, a mass ratio of calcium powder to pyrite powder is 1:4, wherein the mineral powder serves as an electron donor to provide an alternative carbon source; and a foaming agent, 2-5 parts; wherein the blowing agents comprises sodium carbonate or azodicarbonamide.

2. The sewage treatment biological agent according to claim 1, wherein the three-dimensional helical structure has a length of 0.5-2.5 mm.

3. A preparation method for the sewage treatment biological agent according to claim 1, comprising:
mixing the induced nucleus and an activated sludge to obtain a mixture;
putting the mixture into a pulse up-flow reactor for membrane formation, hydraulic sieving and granulation to obtain the sewage treatment biological agent.

4. The preparation method according to claim 3, wherein a sewage in the pulse up-flow reactor enters the pulse up-flow reactor in a pulse manner after being oxygenated and aerated, wherein before being oxygenated and aerated the sewage has a COD of 100 mg/L-400 mg/L, an ammonia nitrogen of 15 mg/L-40 mg/L, and a total nitrogen of 15 mg/L-45 mg/L.

5. The preparation method according to claim 3, wherein the preparation method
further comprises forming a flow shear force from the bottom to the top in the pulse up-flow reactor by pulse inflow of 5 s/time to 40 s/time.

6. The sewage treatment biological agent according to claim 1, wherein the preparation raw materials of the induced nucleus comprise: hydrophilic surface modifiers; polyols, quaternary ammonium salts and sulfonates.

7. The sewage treatment biological agent according to claim 1, wherein the three-dimensional helical structure has pores distributed thereon.

* * * * *